United States Patent
Mason

(10) Patent No.: US 8,414,530 B2
(45) Date of Patent: Apr. 9, 2013

(54) VASCULAR ACCESS DEVICE

(76) Inventor: Roger Alan Mason, Port of Spain (TT)

( * ) Notice: Subject to any disclaimer, the term of this patent is extended or adjusted under 35 U.S.C. 154(b) by 0 days.

(21) Appl. No.: 13/055,823

(22) PCT Filed: Jul. 27, 2009

(86) PCT No.: PCT/US2009/051856
§ 371 (c)(1),
(2), (4) Date: Apr. 14, 2011

(87) PCT Pub. No.: WO2010/011995
PCT Pub. Date: Jan. 28, 2010

(65) Prior Publication Data
US 2011/0184347 A1    Jul. 28, 2011

Related U.S. Application Data

(60) Provisional application No. 61/083,677, filed on Jul. 25, 2008.

(51) Int. Cl.
*A61M 5/00* (2006.01)
(52) U.S. Cl. ...................................................... 604/117
(58) Field of Classification Search .................. 604/115, 604/116, 117, 174, 175, 288.01, 288.02
See application file for complete search history.

(56) References Cited

U.S. PATENT DOCUMENTS

| 4,164,221 | A | * | 8/1979 | Bentley et al. | 604/513 |
|---|---|---|---|---|---|
| 4,645,495 | A |   | 2/1987 | Vaillancourt |  |
| 4,822,341 | A | * | 4/1989 | Colone | 604/175 |
| 5,104,400 | A |   | 4/1992 | Berguer et al. |  |
| 5,176,653 | A | * | 1/1993 | Metals | 604/167.02 |
| 5,695,470 | A | * | 12/1997 | Roussigne et al. | 604/116 |
| 5,911,734 | A |   | 6/1999 | Tsugita et al. |  |
| 7,261,705 | B2 | * | 8/2007 | Edoga et al. | 604/288.02 |
| 2009/0076466 | A1 | * | 3/2009 | Quebbemann et al. | 604/288.02 |
| 2010/0063461 | A1 | * | 3/2010 | Esteve | 604/288.02 |

OTHER PUBLICATIONS

Notification Concerning Transmittal of International Preliminary Report on Patentability (Chapter 1 of the Patent Cooperation Treaty), issued on Feb. 3, 2011, in connection with related International Application No. PCT/US2009/061856.
International Search Report, dated Sep. 17, 2009, in PCT/US2009/051856.

\* cited by examiner

*Primary Examiner* — Aarti B Berdichevsky
(74) *Attorney, Agent, or Firm* — Venable LLP; Jeffri A. Kaminski; Ryan M. Flandro

(57) ABSTRACT

A vascular access device may comprise a thin polymer patch configured to be attached to a wall of a vein. The vascular access device may also include a main body including a first end and a second end. The main body may have an inner surface defining a cavity extending between openings at the first and second ends along an axis. The first end of the main body may be connected to the polymer patch, and the cavity may taper between the second end and the first end. The vascular access device may include a cap connected to the second end of the main body. The vascular access device may also include a fluid sealed within the cavity. When the vascular access device is implanted in a patient and a dialysis needle is received in the cavity, the needle may be guided by the inner surface toward the wall of the vein.

14 Claims, 2 Drawing Sheets

VASCULAR ACCESS DEVICE

This application claims the priority benefit of U.S. Provisional Patent Application No. 61/083,677, filed Jul. 25, 2009, and entitled "Vascular Access Device," the entirety of which is hereby incorporated by reference.

BACKGROUND

1. Field of Invention

The invention is related to a subcutaneously implanted vascular access device including a main body having a tapered, fluid-filled cavity. The invention is also related to a vascular access device including a percutaneously placed catheter.

2. Related Art

End stage renal failure patients require repeated, chronic access to their vascular system to allow life sustaining hemodialysis. In the United States, an estimated 250,000 patients per year undergo hemodialysis and, thus, require maintenance of a vascular access site. The estimated cost associated with this procedure is approximately $8000 dollars per year per person. Cumulatively, 2 billion US dollars/year are spent.

Current vascular access systems have limitations that commonly lead to system failure requiring interventions to reestablish access. There are three commonly-used systems to establish vascular access for kidney failure patients.

Catheter-based access. This system may include a synthetic catheter that may be placed transcutaneously. Alternatively, the catheter may have an attached buried reservoir that allows the dialysis machine operator to attach the patient's catheter to the hemodialysis machine. Although this system offers immediate availability for use after placement, there may be several disadvantages. First, the system may be prone to infection, particularly for transcutaneously placed catheters where infection can develop at the skin exit site. The presence of a foreign body in the vascular system is prone to seeding from inadvertent "breaks in sterile technique" as technicians repeatedly access the system to place patients on the dialysis machine as well as seeding from distant sources of infection in the patient via the bloodstream. When a catheter becomes infected, removal is usually required to clear the infection. As a result, another catheter must be placed at another site to resume treatment. This requirement results in the additional cost and inconvenience of performing an additional surgical procedure as well as the cost of the replacement catheter.

Second, the relatively small caliber of the synthetic tubes placed in the vascular system may permit only limited blood flow through the system while a patient is on the dialysis machine. This may prolong the time each patient needs to be dialyzed and may indirectly contribute to the frequency of dialysis treatments.

Third, the catheter system introduces a foreign body in a central vein. This can lead to further complications including, for example, frequent formation of fibrin clots or blood clots in the lumen of the tube requiring the infusion of costly thrombolytic drugs to clear the tubes. Sometimes even more costly endovascular procedures are required to reestablish function in a catheter. Furthermore, the foreign body tube in the vascular system may result in a thrombosis or a narrowing (stenosis) of a major vein (subclavian vein or superior vena cava) that then precludes using that vein for future venous access in that patient. This complication can have life threatening ramifications particularly if the stenosis involves the superior vena cava.

Native Arterial Venous Fistula. A second mode of vascular access requires the construction of a connection or arterial venous (AV) fistula between a patient's native vein and an adjacent artery that creates a high flow of blood through a limited portion (generally 15-20 cm) of the patient's vascular system. This superficially positioned natural vascular conduit usually grows to a certain minimal size (approximately 5-6 mm or greater in diameter) that then provides a target for the dialysis technician to insert the two needles that are required to place a patient on the dialysis machine. Some advantages of a natural AV fistula may include, for example, longevity, immunity from infection, and low cost. This type of fistula has the longest life span of all known types of vascular access, lasting from several years up to twenty years or more, with the possibility of performing a secondary surgical intervention to salvage the functioning of the fistula even if complications do develop with the fistula over time. Also, since the fistula is constructed of "native tissue," it is relatively immune to infection. Moreover, the fistula is cheaper to construct since there is no requirement for a costly catheter or synthetic graft.

On the other hand, since there are limited sites for the creation of a functioning fistula in each patient, the current standard of care is to perform the fistula in the most distal vessels in a patient's upper extremity where a preoperative assessment indicates that the fistula has a reasonable chance for maturing successfully. A 20% failure rate is considered acceptable for "first time" fistulas as vascular access surgeons try to maximize the available sites in a patient cognizant that patients may require new fistulas at other sites in the future if the primary fistula eventually fails. This 20% failure rate can lead to further operations and, thus, significant additional costs and inconvenience to the patient.

Access to a fistula is highly dependent on the skill of the dialysis technician. A fistula that, at maturation, is somewhat smaller than desirable, or is located deeper in the patient's tissues presenting a less easily palpable target than normal, is more likely to be damaged during attempts to access the fistula. Native fistulas can be damaged in a variety of ways. Repeated access through nearby adjacent sites can lead to localized trauma to the wall of the fistula causing a weakening or "ballooning out" of the wall of the fistula. This local aneurysm can lead to a failure of the fistula if not repaired. Also, if the technician inadvertently punctures the "back wall" of the fistula while trying to gain access through the "front wall," or if inadequate pressure is held over a needle access site at the end of the dialysis run, a local collection of blood (called a hematoma) can form that, at the least, can prevent access to the fistula over the next several weeks in that same location. At worst, the blood collection can progress to form an organized scar that constricts the fistula, possibly leading to its ultimate failure.

In the United States, the preferred method that is taught to access native fistulas is the step ladder approach, i.e., constantly moving the locations where the two access needles are placed in the fistula. The protocol of sticking needles into the fistula at different locations at each dialysis session leads to increased pain experienced by the patient since the effect of a localized area of insensitive scar tissue—e.g., where the fistula is accessed using the "buttonhole" technique (discussed further below)—is never allowed to form. Moreover, the native fistula may require at least 4 weeks and sometimes up to several months to "mature," i.e., to grow to an adequate size and increased thickness of its walls that will allow the vessel to be safely punctured with a needle.

The "buttonhole" technique to access fistulas, favored in Europe, has been shown in limited studies to increase the longevity of a fistula while decreasing complications associated with moving access sites to different locations in the fistula during subsequent dialysis sessions. Some advantages of the "buttonhole" technique may include: (a) two nearby needle puncture points to access the fistula (approximately 3 cm apart) require only a relatively short functioning and accessible fistula to access the bloodstream; (b) the scar tissue that develops from repeated puncture of the skin in two locations causes a relative insensitivity of the skin to puncture pain; (c) the narrow cicatricial tract self seals relatively easily with thrombus after removal of the needles following a dialysis run, decreasing the incidence of perifistula hematomas that can temporarily, or even permanently, incapacitate a fistula; and (d) after a cicatricial track has been established, "blunt" needles can be used to access the graft, decreasing the incidence of needle point damage to the back wall of the fistula when inserting needles.

A disadvantage of the "buttonhole" approach is the logistical problem that requires a highly skilled dialysis technician to create a "button-hole" track. Ideally, a single highly-skilled technician will repetitively perform the needle insertion on the same patient during the initial dialysis sessions, following the exact needle track in the same patient (same entrance point, same angle, same depth) every time for the first 10-15 access events until a well formed tract has developed. The logistical difficulty of having the same highly-skilled technician available for the first 10-15 access events in an individual patient currently limits the wider applicability of this technique.

Synthetic Bridge Graft Fistula. A third mode of vascular access requires the placement of a synthetic graft in a subcutaneous position, usually in a patient's upper extremity. The technician achieves access to the vascular system by placing needles directly into the easily palpable graft. Some advantages may include that the graft provides a reliable, easily accessible conduit to access to connect a patient to the dialysis machine. This choice of access is particularly valuable in patients who do not have the requisite minimally sized vein that will permit the establishment of a "native" AV fistula.

On the other hand, the cost of such a graft is approximately $500 (US) per patient. Also, the most commonly placed grafts require several days and up to several weeks for perioperative swelling to decrease and for the grafts to become sufficiently incorporated into a patient's tissues to allow safe access via the graft. The graft can also become infected by inadvertent "lapses of sterile technique" by the dialysis technician or through seeding from distant sources in the patient. An infected graft frequently requires a very costly and inconvenient (to the patient) series of procedures that includes removal of the infected graft, placement of an interim dialysis catheter, and a subsequent implantation of a new graft after the infection has been definitively treated to reestablish vascular access. A synthetic graft can also be prone to development of early or late thrombosis—due its synthetic "foreign" quality.

Moreover, the site of the venous anastomosis between the graft and the patient's native vein can be a frequent site of stenosis that develops from a mismatch in the distensibility characteristics of the patient's native vein and the synthetic graft. This can require secondary costly surgical or endovascular interventions to correct the problem and to preserve continued functioning of the graft as a viable access conduit. Some grafts may even form a stenosis within the graft due to a proliferation of fibrin and scar tissue that requires a secondary procedure to maintain the viability of the graft. Additionally, repeated puncture of a graft in the same location by the dialysis technician can lead to a "pseudoaneurysm" formation (i.e., a localized collection of blood) that can eventually lead to failure of the graft if not corrected. Improper technique by the dialysis technician can also result in a hematoma formation during access to the graft or following removal of the needles at the end of the dialysis run. The hematoma may make access to the graft in that location difficult or impossible for a period of time, and may lead to occlusion of the graft.

Vascular access devices are needed that substantially overcome the foregoing disadvantages.

SUMMARY

A vascular access device according to an embodiment of the invention may provide repetitive access to, for example, a native AV fistula or an AV fistula synthetic graft.

In an embodiment of the invention, a vascular access device for subcutaneous implantation may comprise a thin polymer patch configured to be attached to a wall of a vein. The vascular access device may also include a main body including a first end and a second end. The main body may have an inner surface defining a cavity extending between openings at the first and second ends along an axis. The first end of the main body may be attached to the polymer patch. The cavity may taper between the second end and the first end. The vascular access device may include a cap (e.g., of polymeric silicone material) connected to the second end of the main body to act as a self-sealing hemostatic barrier. The vascular access device may also include fluid sealed within the cavity. When the vascular access device is implanted in a patient and a dialysis needle is received in the cavity, the needle may be guided by the inner surface toward the wall of the vein.

Further features and advantages of the invention, as well as the structure and operation of various embodiments of the invention, are described in detail below with reference to the accompanying drawings.

BRIEF DESCRIPTION OF THE DRAWINGS

The foregoing and other features and advantages of the invention will be apparent from the following, more particular description of some example embodiments of the invention, as illustrated in the accompanying drawings wherein like reference numbers generally indicate identical, functionally similar, and/or structurally similar elements. Unless otherwise indicated, the accompanying drawing figures are not to scale.

DETAILED DESCRIPTION

Figure 1:
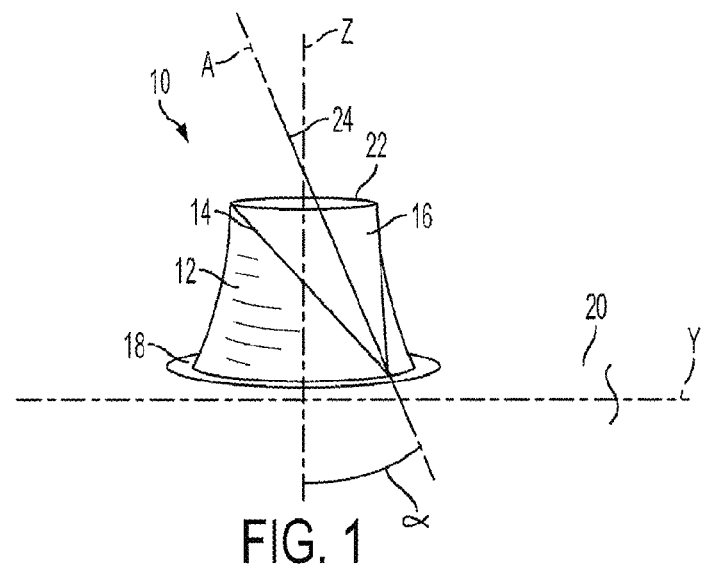
FIG. 1 depicts a schematic and illustrative side view of a vascular access device according to an embodiment of the invention.

Various embodiments of the invention are discussed in detail below. While specific embodiments are discussed, specific terminology is employed for the sake of clarity. However, the invention is not intended to be limited to the specific terminology so selected and it should be understood that this is done for illustration purposes only. A person skilled in the relevant art will recognize that other components and configurations can be used without parting from the spirit and scope of the invention. Each specific element includes all technical equivalents that operate in a similar manner to accomplish a similar purpose.

In the following description of some embodiments of the invention, directional words such as, for example, "top," "bottom," "left," "right," "upwardly," and "downwardly," are employed by way of description and not limitation with respect to the orientation of the device and its various components as illustrated in the drawings.

FIG. 1 depicts a schematic and illustrative side view of a vascular access device 10 according to an embodiment of the invention. The vascular access device 10, which may be a part of a vascular access kit including a telescopic needle assembly, may facilitate easier access to a patient's vascular system by, for example, lower level skilled technicians. The vascular access device 10 may include a main body 12 which may be formed of a biocompatible material such as, for example, but not limited to, a biocompatible plastic material. An inner surface 14 of the main body 12 may define a funnel—or cone-shaped tapered interior cavity 16 extending between openings at a first end and a second end along an oblique axis A. The tapered inner surface 14 may be defined by, for example, a funnel-shaped insert (e.g., of metal) received in the main body 12 and may be configured to guide a dialysis access needle 24 toward the narrow opening at the first end.

The first end of the main body 12 may be coupled or connected to a thin polymer patch 18. The polymer patch 18 may be formed of a suitable material such as, for example but not limited to, polytetrafluoroethylene (PTFE) film, for being secured to a wall of a vein or AV fistula 20. A thin, flexible cap or seal 22 may be attached to the second end of the main body 12. The cap 22 may be formed, for example, from a thin polymeric silicone material. A fluid such as, for example, but not limited to, heparinized saline, may be sealed within the cavity. When the vascular access device 10 is implanted in a patient (i.e., secured to the wall of a vein 20 by the polymer patch 18) and a dialysis needle 24 is received in the cavity 16 through the cap 22, the needle 24 may be guided by the inner surface 14 of the cavity 16 toward a point on the wall of the vein 20 at an angle α along axis A. In the embodiment of the inventions shown in FIG. 1, an axis Y may extend along the lumen of the vein 20 and an axis Z may extend normal to axis Y. The angle α may be defined relative to axis Z such that the needle 24 is oriented approximately 30 degrees towards arterial inflow when the needle 24 is fully inserted into the vein or fistula 20.

Figure 2:
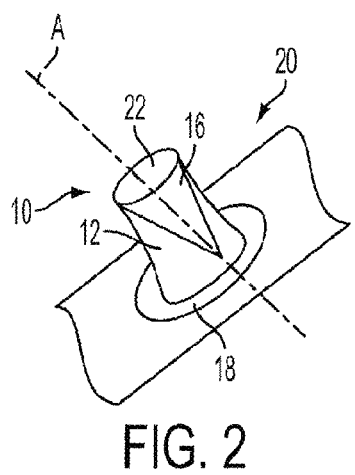
FIG. 2 depicts a schematic and illustrative perspective view of the vascular access device of FIG. 1.
Figure 3:
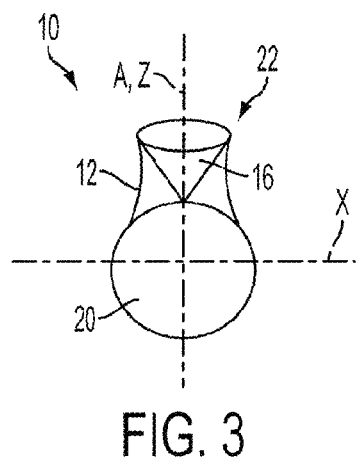
FIG. 3 depicts a schematic and illustrative cross-sectional view of the vascular access device of FIG. 1.

FIG. 2 depicts a schematic and illustrative perspective view of the subcutaneously implanted vascular access device 10 of FIG. 1 showing the main body 12 attached to an outer wall of the vein 20 via the polymer patch 18. FIG. 3 depicts a schematic and illustrative cross-sectional view of the subcutaneously implanted vascular access device 10 of FIGS. 1-2.

Example Protocol for Vascular Access Device and System:

A preoperative duplex study may identify a 3 mm or greater diameter vein (most commonly the cephalic vein) and a suitable radial artery (e.g., having a 2 mm or greater diameter and relatively free of arteriosclerotic disease) in the forearm of a potential patient.

The patient may be heparinized with standard systemic heparinization and an arteriovenous anastomosis, 10-15 mm in length, may then be constructed. A site may be selected 2.5 cm from the arterial anastomosis where the vascular (arterial) access device 10 (see FIGS. 1-3) may be attached to the vein 20 to create a 30 degree orientation of the port in the direction of arterial inflow along the vein 20. The vascular access device 10 may be fixed to the newly constructed AV fistula 20 using one of two techniques:

(a) The main body 12 of the vascular access device 10, which may be fused to a small oval patch 18 of PTFE, may be attached to the external surface of the vein 20 using, for example, a standard bio-glue after distending an isolated segment of the fistula 20 with heparinized saline solution. The advantage of this technique is that it doesn't alter the native endothelial anatomy of the internal fistula wall limiting the risk of platelet agglutination that may lead to localized intimal hyperplasia and eventual stenosis. It most closely duplicates the access physiology created by the traditional buttonhole technique for fistula access with all of its attendant advantages, and without its disadvantage (requiring a skilled dialysis technician) to ensure its success.

(b) Alternatively, a one centimeter venotomy can be made in the vessel 20 and the PTFE thin patch graft 18, bonded to the main body 12 of the device 10, can be fixed to the venotomy using clips or suture. This technique presents an exposed PTFE surface to fistula blood flow and may increase the incidence of localized stenosis due to flow turbulence and a foreign body surface, but the technique may be useful particularly in a small vein where a patch angioplasty may promote long term patency of the fistula.

The vascular access device 10 may include one of two differently designed ports depending on arterial or venous access. For example, one port may be for arterial access and may be designed to orient the needle point 30 degrees towards arterial inflow when the needle is fully inserted into the fistula. Alternatively, for example, the venous port may be designed to direct the needle 30 degrees from the parallel for effluent venous blood flow.

Figure 5:
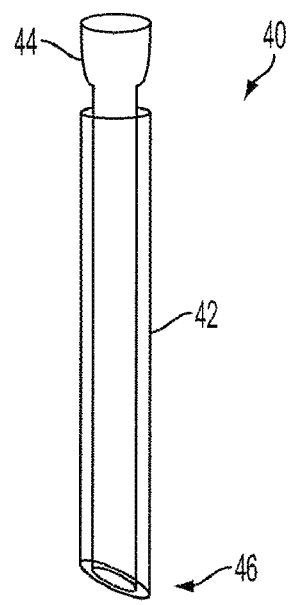
FIG. 5 depicts a schematic and illustrative view of a "needle within a needle" access needle.

A vascular access kit may include the vascular access device 10 as shown in the embodiments depicted in FIGS. 1-3 and may also include a telescopic (i.e., "needle within a needle") dialysis access needle 40 as shown, for example, in FIG. 5. The design of the vascular access device 10 as shown, for example, in FIGS. 1-3, may present an easy target for a midlevel technician to access using the following technique after standard skin sterilization:

(a) The operator may pierce the skin "buttonhole" target with a specially designed "needle within a needle" access device 40. The needle within a needle configuration 40 (see FIG. 5) may be designed to permit an internal needle 44 to slide within an outer needle 42 to allow its tip to be advanced beyond the tip 46 of the outer needle 42. Both needles 42, 44 may be hollow bore and a synthetic plastic seal (not shown), e.g., of a polymeric silicone material, at the proximal end of the outer needle 42 may avoid leakage of fluid between the needles 42, 44.

(b) The outer needle 42 may be, for example, but not limited to, a 16 gauge needle containing a slightly smaller diameter hollow bore needle 44 within it. The access needle 40 may be used to access the cavity 16 of the vascular access device 10 using local anesthesia to anesthetize the skin for the first 10-15 penetrations until an insensitive cicatrix has formed.

(c) The operator, with suction maintained on a syringe attached to the internal needle 44, may advance the "needle within a needle assembly" 40 until the flush needle points 46 penetrate the surface of the silicone elastomer membrane 22 (e.g., the plastic cap) attached at the second end of the main body 12 of the subcutaneously implanted vascular access device 10.

(d) After fluid is aspirated into the attached syringe, a spring activated clip "wing" (not shown) mounted on the body of the outer needle 42 may be advanced to the surface of the skin where it fixes the outer needle 42 avoiding further penetration of the outer needle 42 below the skin. The internal needle 44 may then be advanced within the outer needle 42 into the cavity 16 of the main body 12 with the funnel-shaped inner surface 14 naturally guiding the point of the internal needle 44 to the exact location in the wall of the vein 20 where fistula puncture is successfully repetitively performed. The internal needle 44 is advanced until a distance equal to the length of the main body 12 of the device 10 has been traversed when a second plastic wing device (not shown), fixed to the internal needle 44, will abut a plastic hub of the outer needle 42 preventing its further advancement. This second plastic wing device (not shown in detail) may be affixed to the plastic hub of the outer needle 42 using a spring device avoiding further advancement of the internal needle 44, locking it in a stationary position. This may ensure an exact ideal depth of needle penetration of the cavity 16 and adjacent vein 20 to avoid damage to the posterior wall of the vein 20 while ensuring proper seating of the needle tip in the fistula lumen. The internal needle 44 may be aspirated to ensure good blood flow. The plastic wings attached to the external needle 42 may be secured to the skin using steristrips with or without benzoin.

(e) At the conclusion of the dialysis, the internal needle 44 may be withdrawn to a mark on the needle 44 (e.g., approximately 5 mm) until the point of the needle 44 is outside the vein lumen 20 and inside the cavity 16. At this point, the operator should not be able to freely aspirate blood through the needle 44. Heparin, 1000 units/cc may then be injected into the reservoir or cavity 16 through the needle 44 after an occluding obturator is removed from the sump channel of the external needle 42 that communicates with the lumen of the external needle 42 at its tip 46. The sump channel may allow a flushing exit for the instillation of heparin through the internal needle 44 into the cavity or reservoir chamber 16 to prevent post use thrombus formation. The needle assembly 40 may be removed after the designated amount of heparin is injected to fill the reservoir chamber 16 with the needle assembly 40 withdrawn during the injection cycle injecting heparin under pressure.

A second venotomy may be made 5 cm from the original venotomy site and a second vascular access device may be anastomosed to the vein with the patch positioned to create a 150 degree orientation along the direction of venous outflow. The devices may be secured to pockets in the subcutaneous tissue to allow easy access by the dialysis technician. The forearm wound may be closed in a standard manner. The access reservoirs and fistula can be accessed immediately for dialysis.

If a patient has no suitable upper extremity veins, the procedure can be performed on lower extremity vein sites, or an AV fistula graft can be placed in the upper extremity with attachment of the vascular access device to the graft.

An advantage of the vascular access system may include, for example but not limited to, immediate access after creation of the fistula (similar to current dialysis catheter access techniques). The reservoir may allow short, wide bore access to the fistula using short, 16 gauge access needles that allow much higher flow rates than standard dialysis catheters markedly reducing duration of dialysis sessions.

The vascular access device design may eliminate the possibility of catheter damage to the major venous drainage systems in the chest caused by the intraluminal position of synthetic catheters in the great veins. If the access ports become infected, or are otherwise rendered dysfunctional, they can be removed and replaced in a different location on the native fistula with repair of the fistula using, for example, a vein patch angioplasty technique or a vein interposition graft. The vascular access device may facilitate the performance of endovascular interventions to treat complications within the fistula such as intimal hypertrophy and stenosis.

The vascular access device may eliminate many of the potential hazards of the known native AV fistula or fistula graft solutions since the fistulas may be, for example, largely protected from potential direct needle damage by the dialysis technicians, thus obviating the following complications: the formation of aneurysms or pseudoaneurysm damage to the fistula wall, the formation of perifistula hematomas, or intimal hyperplasia leading to stenosis. Also, the hazards of infection with a synthetic graft, or the risk of distal synthetic graft/vein anastomotic stenoses may be largely eliminated. Also, continuously increased flow in the native vessel (e.g., the AV fistula) may allow natural increase in the size and flow rate of the native vessel. Since the vascular access device may be attached to a newly created fistula, there may not be a deficit created if the device fails. Furthermore, since the patient's fistula naturally enlarges as it matures, there should be no steal created in the normal distal distribution territory of the donor artery, particularly if the radial artery is used as the donor artery. Furthermore, if the fistula fails completely, the function of the donor artery is usually unaffected.

Therefore, the vascular access device may provide a very significant saving of patient lives due to more efficient access for hemodialysis, as well as huge cost savings with a lower requirement for the creation of new fistulas, a much lower requirement for placement of new graft fistulas and for the placement of temporary or permanent dialysis catheters.

Figure 4:
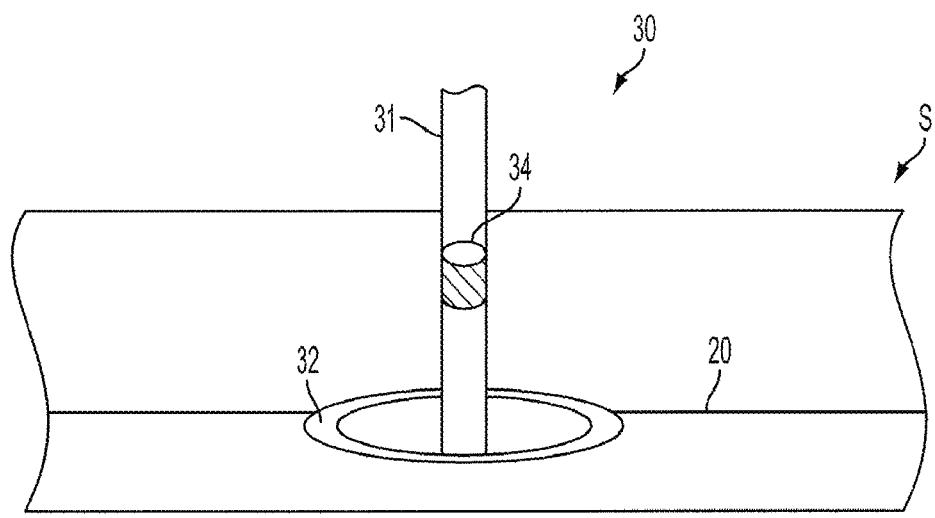
FIG. 4 depicts a schematic and illustrative side view of a vascular access device according to another embodiment of the invention.

FIG. 4 depicts a schematic and illustrative side view of a vascular access device 30 according to another embodiment of the invention. According to the embodiment depicted in FIG. 4, AV access may be achieved by attaching a percutaneous catheter 31 onto the wall of a previously constructed AV fistula 20.

A second vascular access option may offer an alternative vascular access technique for patients who cannot tolerate repeat percutaneous access to the subcutaneously implanted vascular access device described above with reference to FIGS. 1-3, and prefer transcutaneous catheters. This device 30 may include a silicone elastomer conduit 31, such as, for example, but not limited to, 12 gauge diameter, that may be fused or attached circumferentially to a polymer patch 32 such as, for example, but not limited to, an oval 6 mm flat heparin impregnated PTFE patch flush with its internal end. After construction of a traditional AV fistula 20, the fistula 20 may be cross clamped to exclude a 5 cm segment approximately 3 cm from the arterial anastomosis.

The occluded segment of the fistula 20 may be punctured and filled with heparinized saline to distend the isolated segment. A small venotomy may be created in the isolated segment and a guidewire (not shown) placed in the lumen of the vein 20. The PTFE patch graft 32 and attached silicone elastomer catheter 31 may then be advanced over the wire until the patch 32 is situated adjacent to the external vein wall 20. A small coaxial distending balloon (not shown) within the catheter 31 is used to distend the segment of vein 20 at the site of the venotomy and Bioglue may be inserted on the adventitial surface of the vein 20 around the venotomy site to secure the vein wall 20 to the PTFE thin wall patch 32 achieving a secure hemostatic seal between the vein 20 and the PTFE patch 32 with its attached silicone elastomer catheter 31. The distending balloon and guide wire are then removed.

Alternatively, the PTFE patch 32 can be fixed to an enlarged 6 mm venotomy site using, for example, vascular clips or standard 7-0 suture (not shown).

The fistula 20 may then be opened and adequate blood flow may be documented through the catheter 31. The catheter 31 may exit through a small 5 mm skin incision using a tunneling device positioning a teflon pledget 34 on the catheter 31 so that the pledget 34 is within approximately 1 cm of the skin exit site.

A second tunneled catheter with PTFE patch may be placed no closer than 4 cm from the original device using similar technique. Standard vascular venous catheter ports may be attached to the silicone elastomer catheters and the catheters flushed with a heparin solution, 1000 units/cc.

This technique may provide the lowest level of technical skill required to access an AV fistula. The technique may have all of the advantages of current central venous catheters (e.g., ease of use, no skin puncture with needle for patient comfort, immediate availability of use, etc.) without many of the disadvantages of current central venous dialysis catheters including, for example, increased resistance from use of relatively long, small diameter conduits danger of intimal hyperplasia, and stenosis in central veins from longstanding indwelling silicone elastomer catheters. Since there is no intraluminal foreign body at the interior endothelial surface of the fistula other than the smooth surface of the PTFE heparin impregnated graft, there is minimal tendency for the fistula to develop localized intimal hyperplasia and stenosis. If the catheter becomes infected, it can be removed and placed at a distant location on the same fistula. The fistula may be repaired with a vein patch angioplasty.

While various embodiments of the present invention have been described above, it should be understood that they have been presented by way of example only, and not limitation. Thus, the breadth and scope of the present invention should not be limited by any of the above-described embodiments, but should instead be defined only in accordance with the following claims and their equivalents.

The invention claimed is:

1. A vascular access device comprising:
    a thin polymer patch configured to be attached to a wall of an artery, a vein, or an AV fistula; and
    a main body including a first end and a second end and having an inner surface defining an oblique conical cavity extending between openings at the first and second ends along an oblique axis,
        wherein the first end of the main body is connected to the polymer patch,
        wherein the oblique conical cavity has an apex and tapers between the second end and the first end along the oblique axis, such that the apex of the oblique conical cavity is adjacent to the first end of the main body, and
        wherein, when the vascular access device is implanted in a patient and a dialysis needle is received in the cavity, the needle is guided by the inner surface toward and through the wall of the artery, vein, or AV fistula.

2. The vascular access device according to claim 1, wherein the main body comprises a biocompatible plastic material.

3. The vascular access device according to claim 1, wherein the inner surface defining the cavity comprises a funnel-shaped metal insert.

4. The vascular access device according to claim 1, wherein the polymer patch comprises polytetrafluoroethylene (PTFE).

5. The vascular access device according to claim 1, further comprising:
    a cap connected to the second end of the main body and covering the opening at the second end.

6. The vascular access device according to claim 5, wherein the cap comprises a polymeric silicone material.

7. The vascular access device according to claim 1, further comprising:
    a fluid sealed within the cavity.

8. The vascular access device according to claim 7, wherein the fluid comprises heparinized saline.

9. The vascular access device according to claim 1, wherein the axis defined by the inner surface of the tapered cavity is provided an angle of approximately 30 degrees to a central axis defined by the main body.

10. A vascular access kit comprising:
    a vascular access device according to claim 1; and
    a telescopically extending needle including
        an outer hollow needle; and
        an internal hollow needle slidably disposed within the outer hollow needle.

11. The vascular access kit according to claim 10, wherein the outer needle comprises an adjustable wing element configured to restrict the extent to which the outer needle is able to extend through skin of the patient.

12. The vascular access kit according to claim 10, wherein the internal needle comprises a wing element configured to restrict the extent to which the internal needle is able to extend beyond a tip of the outer needle.

13. The vascular access device according to claim 1, wherein the axis of the oblique conical cavity is at an angle relative to a direction of blood flow through the artery, vein, or AV fistula to which the polymer patch is attached.

14. The vascular access device according to claim 13, wherein the angle is approximately 30 degrees from an axis perpendicular to the direction of blood flow.

* * * * *